US008816091B2

(12) United States Patent
Dalziel et al.

(10) Patent No.: US 8,816,091 B2
(45) Date of Patent: Aug. 26, 2014

(54) CRYSTALLINE FORMS OF AN 8-AZABICYCLO[3.2.1]OCTANE COMPOUND

(71) Applicants: Sean Dalziel, San Francisco, CA (US); Leticia M. Preza, San Francisco, CA (US); Miroslav Rapta, San Carlos, CA (US); Pierre-Jean Colson, San Francisco, CA (US)

(72) Inventors: Sean Dalziel, San Francisco, CA (US); Leticia M. Preza, San Francisco, CA (US); Miroslav Rapta, San Carlos, CA (US); Pierre-Jean Colson, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 13/965,691

(22) Filed: Aug. 13, 2013

(65) Prior Publication Data

US 2014/0080856 A1 Mar. 20, 2014

Related U.S. Application Data

(62) Division of application No. 13/550,781, filed on Jul. 17, 2012, now Pat. No. 8,536,335, which is a division of application No. 13/081,162, filed on Apr. 6, 2011, now Pat. No. 8,247,555, which is a division of application No. 12/072,534, filed on Feb. 27, 2008, now Pat. No. 7,943,772.

(60) Provisional application No. 60/904,090, filed on Feb. 28, 2007.

(51) Int. Cl.
| C07D 221/02 | (2006.01) |
| A61K 45/06 | (2006.01) |
| A61K 31/485 | (2006.01) |
| C07D 451/02 | (2006.01) |
| A61K 31/46 | (2006.01) |

(52) U.S. Cl.
CPC .............. *C07D 451/02* (2013.01); *A61K 45/06* (2013.01); *A61K 31/485* (2013.01); *A61K 31/46* (2013.01)
USPC ........................................................ 546/221

(58) Field of Classification Search
USPC ........................................................ 546/112
See application file for complete search history.

(56) References Cited

U.S. PATENT DOCUMENTS

| 5,159,081 | A | 10/1992 | Cantrell et al. |
| 6,313,312 | B1 | 11/2001 | Banks et al. |
| 6,469,030 | B2 | 10/2002 | Farrar et al. |
| 6,479,516 | B1 | 11/2002 | Gibson et al. |
| 6,593,348 | B2 | 7/2003 | Carroll et al. |
| 6,610,711 | B2 | 8/2003 | Armer et al. |
| 6,992,090 | B2 | 1/2006 | Le Bourdonnec et al. |
| 7,049,335 | B2 | 5/2006 | McHardy et al. |
| 7,056,930 | B2 | 6/2006 | Coe et al. |
| 7,087,749 | B2 | 8/2006 | Dolle et al. |
| 7,241,887 | B2 | 7/2007 | Coe et al. |
| 7,622,508 | B2 | 11/2009 | Long et al. |
| 8,247,555 | B2 * | 8/2012 | Dalziel et al. ............... 546/112 |
| 8,263,618 | B2 | 9/2012 | Long et al. |
| 8,536,335 | B2 * | 9/2013 | Dalziel et al. ............... 546/112 |
| 2002/0025948 | A1 | 2/2002 | Banks et al. |
| 2004/0186135 | A1 | 9/2004 | Dolle et al. |
| 2004/0204453 | A1 | 10/2004 | McHardy et al. |
| 2013/0158060 | A1 | 6/2013 | Long et al. |

OTHER PUBLICATIONS

Le Bourdonnec et al., "Elucidation of the Bioactive Conformation of the N-Substituted trans-3,4-Dimethyl-4-(3-hydroxyphenyl)piperidine Class of μ-Opioid Receptor Antagonists", Journal of Medicinal Chemistry, vol. 49, pp. 7278-7289 (2006).

Le Bourdonnec et al., "Synthesis and Pharmacological Evaluation of Novel Octahydro-1H-pyrido[1,2-a]pyrazine as μ-Opioid Receptor Antagonists", Journal of Medicinal Chemistry, vol. 49, pp. 7290-7306 (2006).

Diaz et al., "SAR and Biological Evaluation of Novel trans-3,4-dimethyl-4-arylpiperidine Derivatives as Opioid Antagonists", Bioorganic & Medicinal Chemistry Letters, vol. 15 pp. 3844-3848 (2005).

* cited by examiner

*Primary Examiner* — Nizal Chandrakumar
(74) *Attorney, Agent, or Firm* — Jeffrey A. Hagenah; Roberta P. Saxon

(57) ABSTRACT

The invention provides a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof. The invention also provides pharmaceutical compositions comprising such crystalline salt forms, methods of using such crystalline salt forms to treat diseases associated with mu opioid receptor activity, and processes useful for preparing such crystalline salt forms.

17 Claims, 3 Drawing Sheets

US 8,816,091 B2

CRYSTALLINE FORMS OF AN 8-AZABICYCLO[3.2.1]OCTANE COMPOUND

CROSS-REFERENCE TO RELATED APPLICATIONS

This application is a divisional application of U.S. Ser. No. 13/550,781, filed Jul. 17, 2012, now U.S. Pat. No. 8,536,335, which is a divisional application of U.S. Ser. No. 13/081,162, filed Apr. 6, 2011, now U.S. Pat. No. 8,247,555 B2, which is a divisional application of U.S. Ser. No. 12/072,534, filed Feb. 27, 2008, now U.S. Pat. No. 7,943,772 B2; which claims the benefit of U.S. Provisional Application No. 60/904,090, filed on Feb. 28, 2007, the disclosures of which are incorporated herein by reference in their entirety.

BACKGROUND OF THE INVENTION

1. Field of the Invention

The invention is directed to crystalline salt forms of an 8-azabicyclo[3.2.1]octane compound which are useful as mu opioid receptor antagonists. The invention is also directed to pharmaceutical compositions comprising such crystalline compounds, methods of using such compounds for treating or ameliorating medical conditions mediated by mu opioid receptor activity, and processes useful for preparing such compounds.

2. State of the Art

Commonly-assigned U.S. Provisional Application Nos. 60/777,962, filed on Mar. 1, 2006, and 60/841,028, filed on Aug. 30, 2006, and U.S. application Ser. No. 11/711,961 disclose 8-azabicyclo[3.2.1]octane compounds that are mu opioid receptor antagonists that are expected to be useful for treating or ameliorating medical conditions mediated by mu opioid receptor activity. In particular, the compound 3-endo-(8-{2-[cyclohexylmethyl-((S)-2,3-dihydroxy-propionyl)amino]ethyl}-8-aza-bicyclo[3.2.1]oct-3-yl)benzamide sulfate is specifically disclosed in these applications as demonstrating mu opioid receptor antagonist activity.

The chemical structure of 3-endo-(8-{2-[cyclohexylmethyl-((S)-2,3-dihydroxy-propionyl)amino]ethyl}-8-aza-bicyclo[3.2.1]oct-3-yl)benzamide (hereinafter compound 1) is shown below:

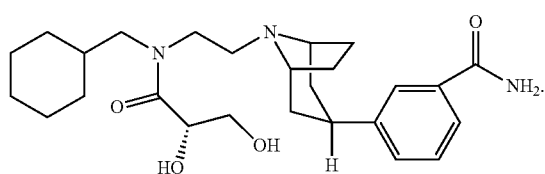

1

To effectively use this compound as a therapeutic agent, it would be desirable to have a solid-state salt form that can be readily manufactured and that has acceptable chemical and physical stability. For example, it would be highly desirable to have a salt form that is thermally stable, for example at temperatures exceeding about 175° C. or about 180° C., and is not hygroscopic nor deliquescent, thereby facilitating processing and storage of the material. Crystalline solids are generally preferred over amorphous forms, for enhancing purity and stability of the manufactured product.

No crystalline salt forms of compound 1 have previously been reported. Accordingly, a need exists for a stable, crystalline salt form of compound 1 that is neither hygroscopic nor deliquescent, and exhibits favorable thermal stability.

SUMMARY OF THE INVENTION

The present invention provides a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof. In one aspect, the crystalline salt form of the invention is a crystalline sulfate salt of compound 1. In another aspect, the crystalline salt form of the invention is a crystalline hydrate of the sulfate salt of compound 1.

Surprisingly, the crystalline sulfate salt of the invention has been found to exhibit no significant thermal events below a melting temperature in the range of about 190 to about 205° C. and to exhibit a weight change of less than about 0.3% when exposed to a range of relative humidity between about 2% and about 90% at room temperature. Furthermore, neither the crystalline sulfate salt of the invention nor the hydrate thereof is deliquescent when exposed to up to about 90% relative humidity at room temperature.

Among other uses, the crystalline salt forms of the invention are expected to be useful for preparing pharmaceutical compositions for treating or ameliorating medical conditions mediated by mu opioid receptor activity. Accordingly, in another of its composition aspects, the invention provides a pharmaceutical composition comprising a pharmaceutically-acceptable carrier and a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof.

The invention also provides a method of treating or ameliorating a disease or condition ameliorated by treatment with a mu opioid receptor antagonist, e.g. a disorder of reduced motility of the gastrointestinal tract, the method comprising administering to the mammal, a therapeutically effective amount of a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof.

The invention further provides a method of treating opioid-induced bowel dysfunction or post-operative ileus, the method comprising administering to the mammal, a therapeutically effective amount of a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof.

In another method aspect, the invention provides a process for preparing a crystalline sulfate salt of the invention, the process comprising contacting 3-endo-(8-{2-[cyclohexylmethyl-((S)-2,3-dihydroxy-propionyl)amino]ethyl}-8-aza-bicyclo[3.2.1]oct-3-yl)benzamide with sulfuric acid to form a reaction mixture, and isolating the crystalline sulfate salt from the reaction mixture.

The invention provides an additional process for preparing a crystalline sulfate salt of the invention, the process comprising dispersing a crystalline hydrate of the sulfate salt of 3-endo-(8-{2-[cyclohexylmethyl-((S)-2,3-dihydroxy-propionyl)amino]ethyl}-8-aza-bicyclo[3.2.1]oct-3-yl)benzamide in a diluent comprising methanol to form a reaction mixture, and isolating the crystalline sulfate salt from the reaction mixture In yet another method aspect, the invention provides a process for preparing a crystalline sulfate salt of compound 1, the process comprising: (a) contacting a protected precursor to compound 1 in which the hydroxy groups are protected, with sulfuric acid to form a first reaction mixture; (b) isolating an intermediate grade solid sulfate salt of compound 1 from the first reaction mixture; (c) dispersing the intermediate grade solid sulfate salt in a diluent comprising methanol to form a second reaction mixture; and (d) isolating the crystalline sulfate salt from the second reaction mixture.

In a related composition aspect, the invention provides the N-cyclohexylmethyl-(2-oxoethyl)-carbamic acid benzyl ester bisulfite adduct, which is useful for the preparation of the above protected precursor to compound 1.

The invention also provides a crystalline sulfate salt of the invention as described herein for use in therapy or as a medicament, as well as the use of a crystalline sulfate salt of the invention in the manufacture of a medicament, especially for the manufacture of a medicament for treating a disorder associated with mu opioid receptor activity in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
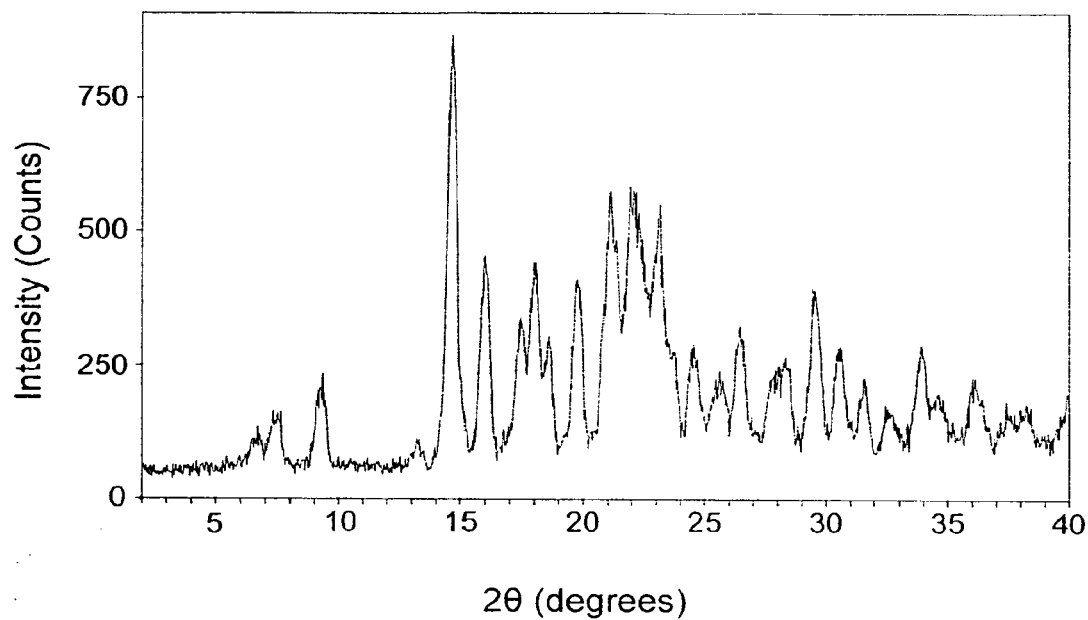
FIG. 1 shows an x-ray powder diffraction (XRPD) pattern of a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

The invention provides a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide or a solvate thereof.

Definitions

When describing the compounds, compositions and methods of the invention, the following terms have the following meanings, unless otherwise indicated.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is specifically termed a hydrate.

The term "crystalline sulfate salt", or alternatively "crystalline sulfate salt (anhydrous form)" or "anhydrous sulfate salt", as used herein means a crystalline solid that does not include a substantially fixed molar fraction of solvent molecules in the crystal lattice, i.e. one that is not a solvate or hydrate. Solvates, or specifically hydrates, of the invention are identified explicitly.

It must be noted that, as used in the specification and appended claims, the singular forms "a", "an", "one", and "the" may include plural references, unless the content clearly dictates otherwise.

Active Agent

The active agent in the present salt forms, i.e. compound 1, is designated 3-endo-(8-{2-[cyclohexylmethyl-((S)-2,3-dihydroxy-propionyl)amino]ethyl}-8-aza-bicyclo[3.2.1]oct-3-yl)benzamide. Alternatively, using the IUPAC conventions as implemented in AutoNom software, (MDL Information Systems, GmbH, Frankfurt, Germany), the compound is denoted 3-((1R,3R,5S)-8-{2-[cyclohexylmethyl-((S)-2,3-dihydroxy-propionyl)amino]ethyl}-8-azabicyclo[3.2.1]oct-3-yl)benzamide. The name used herein therefore corresponds to the IUPAC notation with the endo orientation of the substituted phenyl group with respect to the 8-azabicyclo[3.2.1]octane group indicated explicitly. In yet other common nomenclatures, the "((S)-2,3-dihydroxy-propionyl)amino" portion of the molecule is variously designated as ((S)-2,3-dihydroxy-1-oxopropyl)amino or ((S)-2,3-dihydroxypropanamido)

Salt Forms of the Invention

In one aspect, the invention provides crystalline 3-endo-(8-{2-[cyclohexylmethyl-((S)-2,3-dihydroxy-propionyl)amino]ethyl}-8-aza-bicyclo[3.2.1]oct-3-yl)benzamide sulfate.

In one aspect, the crystalline sulfate salt of the present invention is characterized by an x-ray powder diffraction (XRPD) pattern having two or more diffraction peaks, including three or more and four or more diffraction peaks, at 2θ values selected from 6.58±0.20, 7.52±0.20, 9.35±0.20, 14.69±0.20, 16.01±0.20, 17.45±0.20, 17.99±0.20, 18.62±0.20, 19.76±0.20, 21.11±0.20, 22.07±0.20, 23.18±0.20, 23.74±0.20, 24.56±0.20, 25.63±0.20, 26.45±0.20, 27.86±0.20, 28.31±0.20, 29.54±0.20, 30.59±0.20, 31.58±0.20, 33.89±0.20, and 36.02±0.20. In particular, in this aspect, the crystalline form is characterized by an x-ray powder diffraction pattern having two or more diffraction peaks, including three or more and four or more diffraction peaks, at 2θ values selected from 14.69±0.20, 16.01±0.20, 21.11±0.20, 22.07±0.20, and 23.18±0.20.

As is well known in the field of powder x-ray diffraction, peak positions of XRPD spectra are relatively less sensitive to experimental details, such as details of sample preparation and instrument geometry, than are the relative peak heights. Thus, in one aspect, a crystalline sulfate salt of compound 1 is characterized by an x-ray powder diffraction pattern in which the peak positions are substantially in accordance with those shown in FIG. 1.

The crystalline sulfate structure has been further characterized by single crystal x-ray diffraction analysis, providing the following lattice parameters: unit cell is orthorhombic with dimensions a=6.8239 Å, b=16.2275 Å, c=24.2021 Å, $\alpha=\beta=\gamma=90°$; cell volume (V) of 2680.0 Å$^3$; calculated density is 1.38 g/cm$^3$; space group is P2$_1$2$_1$2$_1$(#19). The resulting molecular structure confirms the chemical composition is that of the sulfate salt of compound 1 in a 1:1 molar ratio of sulfate counterion to compound 1 and that the asymmetric unit cell does not contain water or other solvent molecules. X-ray powder diffraction peaks predicted from the derived atomic positions are in excellent agreement with the observed XRPD pattern.

In another aspect, the crystalline sulfate salt of the present invention is characterized by its behavior when exposed to high temperature. As demonstrated in FIG. 2, the differential scanning calorimetry (DSC) trace of a highly crystalline sample exhibits a peak in endothermic heat flow, identified as a melt transition, in the range of about 190° C. to about 205° C. The thermal gravimetric analysis (TGA) trace shows no significant weight loss at temperatures below the melting point. Thermal decomposition occurs approximately upon melting.

In yet another aspect a crystalline sulfate salt is characterized by its infrared absorption spectrum which shows significant absorption bands at about 430, 590, 639, 705, 867, 1036, 1053, 1105, 1171, 1231, 1277, 1375, 1391, 1452, 1476, 1553, 1596, 1639, 1664, 2852, 2907, 2928, 2967, 3168, and 3357 cm$^{-1}$.

Figure 3:
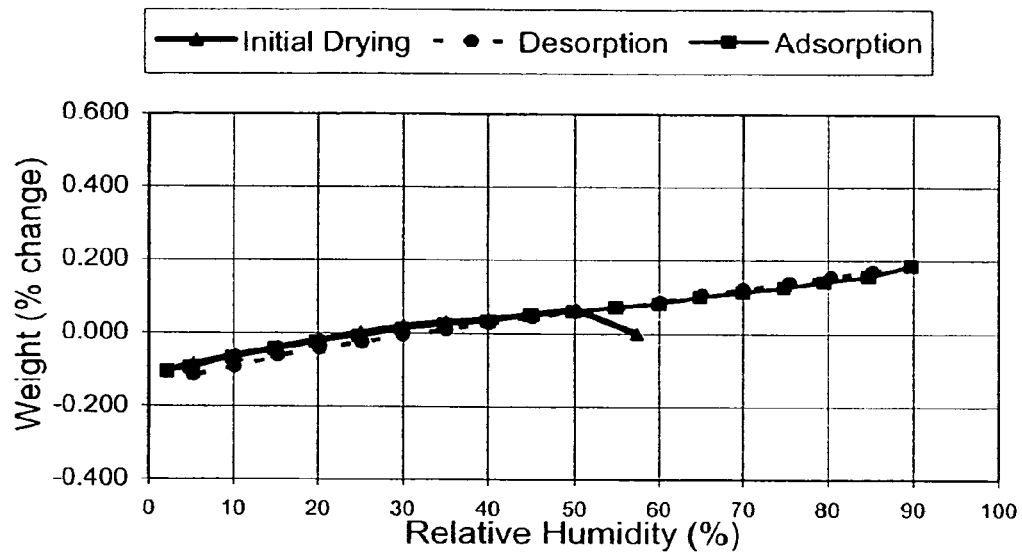
FIG. 3 shows a dynamic moisture sorption (DMS) trace for a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

A crystalline sulfate salt of compound 1 has been demonstrated to have a reversible sorption/desorption profile with an exceptionally low level of hygroscopicity (i.e., less than about 0.3% weight gain in the humidity range of 2% relative humidity to 90% relative humidity at room temperature) as shown in FIG. 3.

Additionally, the crystalline sulfate salt of compound 1 has been found to be stable upon exposure to elevated temperature and humidity. After storage for 4 weeks at 40° C. and 75% relative humidity, analysis by HPLC showed no chemical degradation and there were no detectable changes in the DSC, TGA, or XRPD results.

In another aspect, the invention provides a crystalline hydrate of a sulfate salt of compound 1.

In one aspect, a crystalline hydrate of a sulfate salt of the present invention is characterized by an x-ray powder diffraction (XRPD) pattern having two or more diffraction peaks, including three or more and four or more diffraction peaks, at 2θ values selected from 9.41±0.20, 9.98±0.20, 15.17±0.20, 16.70±0.20, 18.59±0.20, 19.46±0.20, 19.91±0.20, 20.63±0.20, 21.35±0.20, 21.89±0.20, 23.00±0.20, 24.20±0.20, 25.40±0.20, 26.03±0.20, 27.44±0.20, 28.46±0.20, 29.45±0.20, 31.22±0.20, 31.82±0.20, 33.17±0.20, 33.56±0.20 and 36.89±0.20. In particular, in this aspect, the crystalline form is characterized by a x-ray powder diffraction pattern having two or more diffraction peaks, including three or more and four or more diffraction peaks, at 2θ values selected from 16.70±0.20, 18.59±0.20, 19.46±0.20, 19.91±0.20, 23.00±0.20, and 24.20±0.20.

Figure 4:
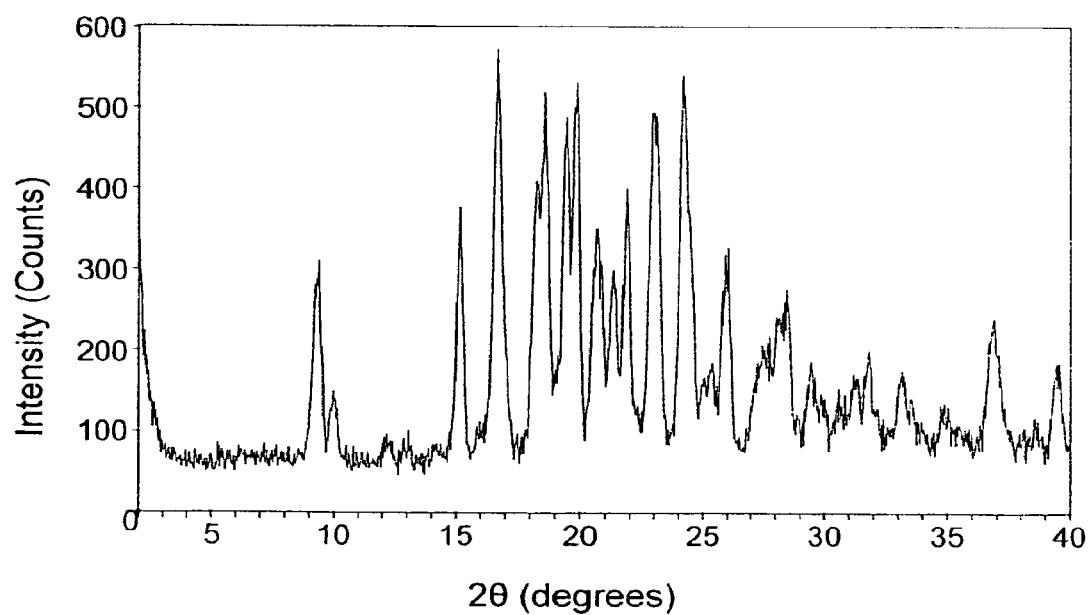
FIG. 4 shows an x-ray powder diffraction (XRPD) pattern of a crystalline hydrate of a sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

In another aspect, a crystalline hydrate of a sulfate salt of compound 1 is characterized by an x-ray powder diffraction pattern in which the peak positions are substantially in accordance with those shown in FIG. 4.

Figure 5:
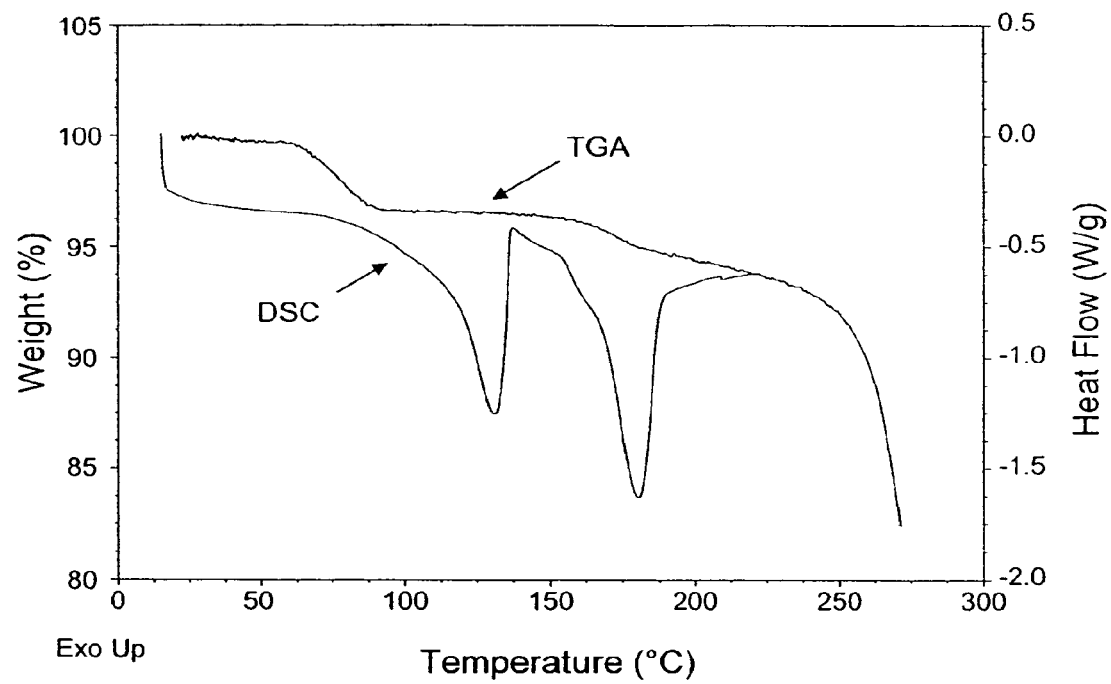
FIG. 5 shows a differential scanning calorimetry (DSC) trace (right side vertical axis) and a thermal gravimetric analysis (TGA) trace (left side vertical axis) for a crystalline hydrate of a sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

The crystalline hydrate of a sulfate salt of the present invention is also characterized by its differential scanning calorimetry (DSC) trace which exhibits two endothermic events: a first peak in endothermic heat flow in the range of about 125 to about 133° C. and a second peak in the range of about 178 to about 183° C. when analyzed at a heating rate of 10° C. per minute as illustrated in FIG. 5. The thermal gravimetric analysis (TGA) trace shows a first thermal event between about 60 and about 140° C. and a second thermal event between about 140 and about 190° C. Analysis by TGA coupled with IR of the material vaporized in the first thermal event is consistent with a hydrate composition having about one mole of water per mole of compound 1 sulfate.

Figure 6:
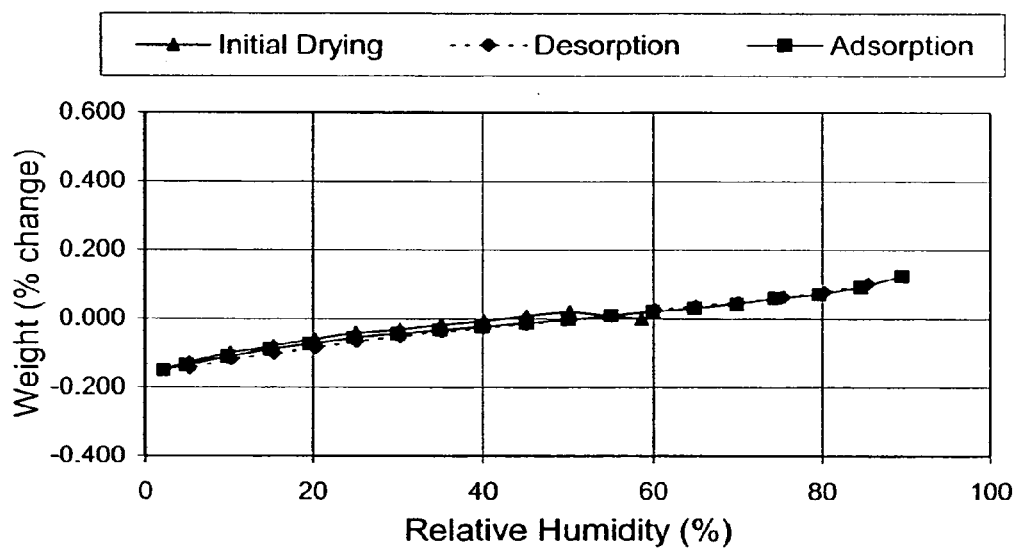
FIG. 6 shows a dynamic moisture sorption (DMS) trace for a crystalline hydrate of a sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

Surprisingly, a crystalline hydrate of a sulfate salt of compound 1 has demonstrated low hygroscopicity. As illustrated in FIG. 6 the crystalline hydrate exhibits a reversible sorption/desorption profile at room temperature over the entire range of about 2% to about 90% relative humidity with less than about 0.3% weight gain over the entire range in relative humidity.

These properties of the salt forms of this invention are further illustrated in the Examples below.

Synthetic Procedures

The active agent, 3-endo-(8-{2-[cyclohexylmethyl-((S)-2,3-dihydroxy-propionyl)amino]ethyl}-8-aza-bicyclo[3.2.1]oct-3-yl)benzamide, can be prepared from readily available starting materials using the procedures described in the Examples below, or using the procedures described in the commonly-assigned U.S. applications listed in the Background section of this application.

In one method of preparation, a crystalline sulfate salt of the invention is prepared by contacting 3-endo-(8-{2-[cyclohexylmethyl-((S)-2,3-dihydroxy-propionyl)amino]ethyl}-8-aza-bicyclo[3.2.1]oct-3-yl)benzamide with about 0.5 to about 1.5 molar equivalents, including about 1 molar equivalent, of sulfuric acid. Generally, this reaction is conducted in an inert diluent at a temperature ranging from about 0° C. to about 65° C., including about 60 to about 65° C. Suitable inert diluents include, for example, methanol, toluene, dichloromethane, and combinations such as toluene and acetonitrile, dichloromethane and acetonitrile, and toluene, acetonitrile, and water, in addition to a methanol and water combination comprising about 10% water. Using these diluents, a reaction mixture with a concentration of between about 5 and about 400 mg/mL, including between about 50 and about 100 mg/mL, is prepared and held for between about 2 and about 24 hours, with optional agitation. The mixture may be cooled to between about 5 and about 20° C. during the holding period.

Upon completion of the reaction, a crystalline salt of the invention is isolated from the reaction mixture by any conventional means, such as filtration, concentration, centrifugation, and the like.

Alternatively, the crystalline sulfate of the invention is prepared by recrystallization of the hydrate form. The crystalline hydrate is dispersed in an inert diluent as described above at a concentration of between about 5 and about 400 mg/ml. Methanol, or a methanol:water combination, in a ratio of from about 3:1 to about 9:1, are particularly useful diluents for this reaction. The reaction mixture is maintained at temperatures in the range of about 0 to about 65° C., typically with agitation, for between about 1 and about 24 hours, including between about 1 and about 6 hours. Typically the reaction mixture is cooled from about 65° C. to between about 5 and about 20° C. during the holding period. To improve the yield, the volume of the solution may be reduced by about 50% before holding the reaction mixture for a time period of between about 1 and about 24 hours, including between about 1 and about 6 hours, at a temperature of between about 5 and about 20° C. The resulting crystals are recovered conventionally.

Both the crystalline sulfate salt and the crystalline hydrate of the sulfate salt of compound 1 are advantageously prepared from the protected precursor of compound 1. As described in the examples below, to prepare the active agent, the protected aldehyde 2, N-cyclohexylmethyl-(2-oxoethyl)-carbamic acid benzyl ester, regenerated from its bisulfite adduct 3, is coupled with 3-endo-(8-azabicyclo[3.2.1]oct-3-yl)-benzamide hydrochloride 4 to provide protected intermediate 5, which is deprotected to provide 3-endo-{8-[2-(cyclohexylmethylamino)ethyl]-8-aza-bicyclo[3.2.1]oct-3-yl}benzamide 6.

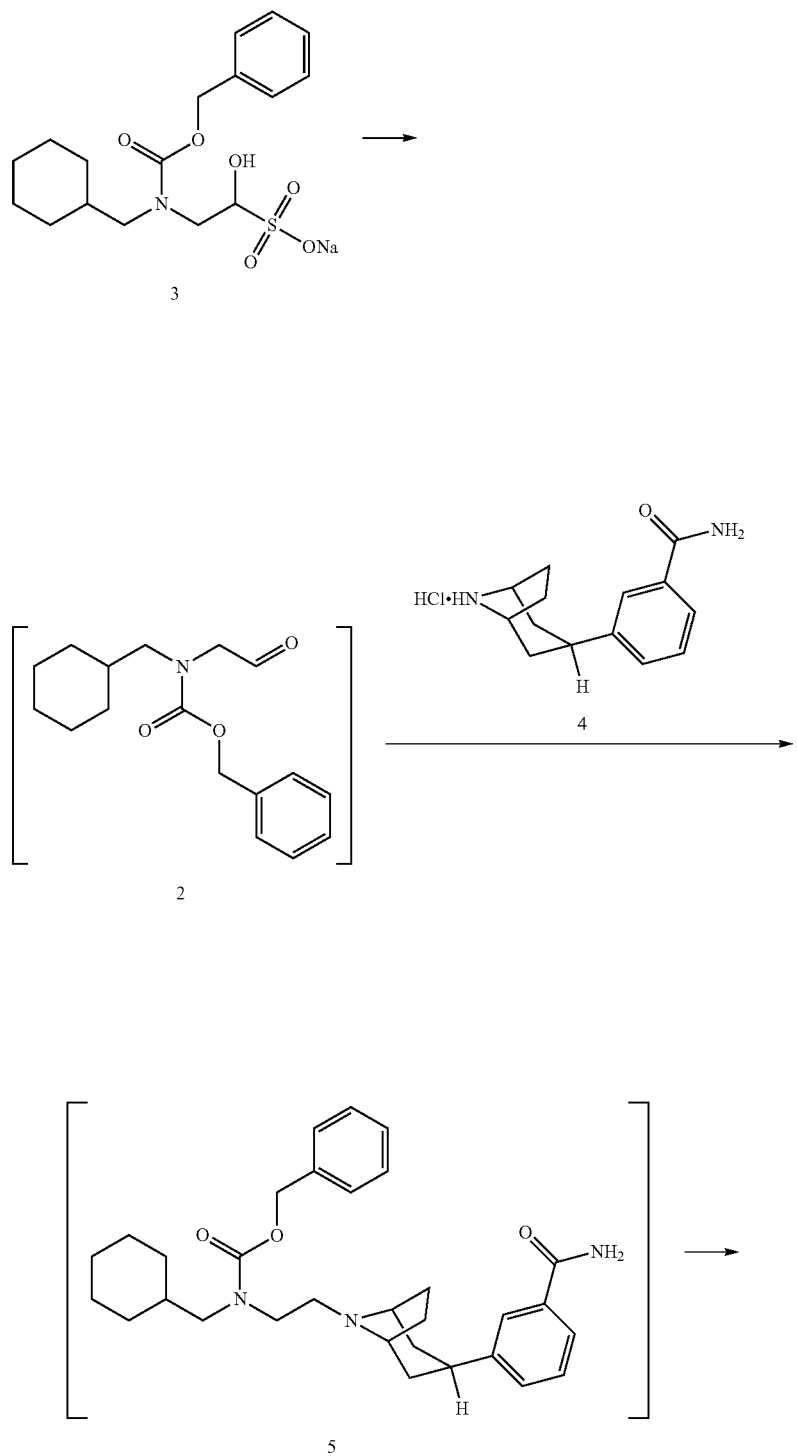

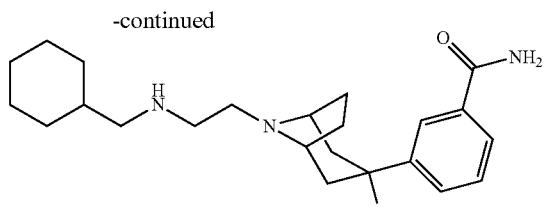

6

Reaction of intermediate 6 with lithium (4S)-2,2-dimethyl-1,3-dioxolane-4-carboxylate 7 provides the protected intermediate (S)-2,2-dimethyl-[1,3]dioxolane-4-carboxylic acid {2-[3-(3-carbamoyl-phenyl)-8-azabicyclo[3.2.1]oct-8-yl]ethyl}cyclohexylmethyl-amide 8

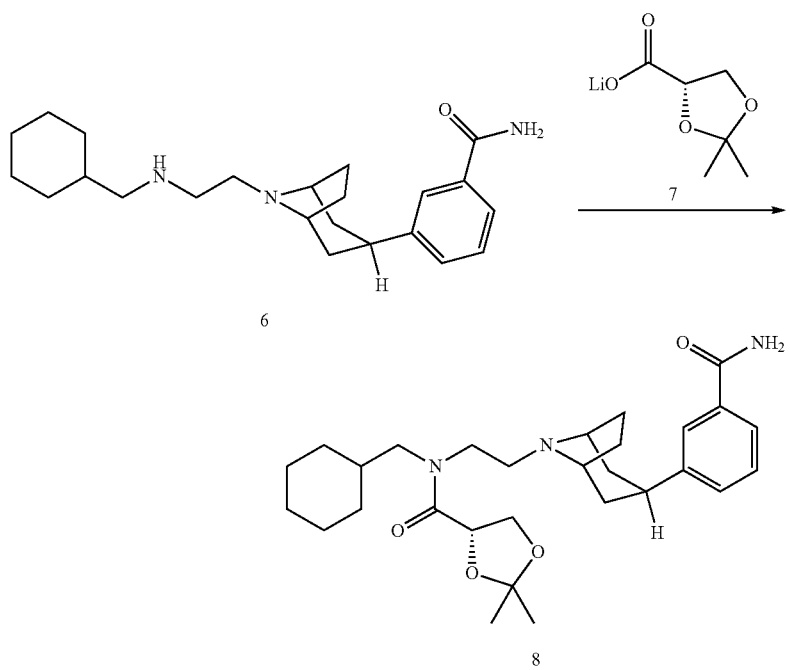

Protected intermediate 8 is contacted with between about 0.8 and about 1.3 equivalents, typically about 1 to about 1.2 equivalents, of aqueous sulfuric acid in an inert diluent, such as ethyl acetate or isopropyl acetate, at a temperature of between about 20 and about 30° C. A second diluent, which is miscible with the reaction mixture, and in which the product is less soluble, is typically included in the reaction mixture. Acetonitrile is useful as the second diluent. The reaction mixture is typically stirred for a period of between about 2 and about 72 hours resulting in deprotection of compound 8 and formation of the intermediate grade solid sulfate salt of compound 1, which is typically predominantly the crystalline hydrate of the sulfate of compound 1. The intermediate grade product can be isolated conventionally, for example by filtration.

The hydrate form may be obtained by recrystallization of the intermediate grade sulfate product, for example, by suspending the intermediate grade product in acetonitrile with heating, adding water to promote dissolution, cooling to ambient temperature, and isolating the recrystallized hydrate form, as described in Example 2 below.

The crystalline sulfate salt of compound 1 may be obtained from the intermediate grade solid product of the deprotection step described above. The intermediate grade product is dispersed in an inert diluent comprising methanol at a concentration between about 5 and about 400 mg/mL, including between about 50 and about 200 mg/mL. Surprisingly, it has been determined that a methanol and water combination, having up to 25% water, including between about 0 and about 15% water, and between about 5 and about 15% water, is a useful diluent for preparing an anhydrous crystalline salt. In particular, a methanol and water combination comprising about 10% water is useful for recrystallization of the intermediate grade product to the anhydrous sulfate salt of the present invention.

In a typical recrystallization process, the reaction mixture is heated until complete dissolution is obtained, for example the reaction mixture is heated to about 65° C., and then cooled to between about 5 and about 22° C. over a period of between about 2 and about 24 hours. Optionally, seed crystals of the anhydrous sulfate salt can be added when the reaction mixture is below the dissolution temperature. The resulting crystals are recovered conventionally, for example, by filtration.

According to yet another process, the hydrate form may be prepared from the crystalline sulfate (anhydrous) form. Typically, the crystalline sulfate is first converted to a more soluble, amorphous form, for example by lyophilization or rapid evaporation of a solution prepared from the crystalline sulfate. The amorphous solid sulfate material is then dispersed in an aqueous solvent system, for example 25% water and 75% acetonitrile and optionally agitated for a time period, greater than about 12 or greater than about 24 hours, at temperatures in the range of about 0 to about 65° C. Typically, the temperature is first raised to about 65° C. and then lowered to between about 5 and about 20° C. The resulting crystalline hydrate form is recovered conventionally.

Accordingly, in a method aspect, among other processes, the invention provides a process for preparing a crystalline sulfate salt of compound 1, the process comprising: (a) contacting a protected precursor to compound 1 in which the hydroxy groups are protected, with sulfuric acid to form a first reaction mixture; (b) isolating an intermediate grade solid sulfate salt of compound 1 from the first reaction mixture; (c) dispersing the intermediate grade solid sulfate salt in a diluent comprising methanol to form a second reaction mixture; and (d) isolating the crystalline sulfate salt from the second reaction mixture.

Further, in a composition aspect, the invention provides the N-cyclohexylmethyl-(2-oxoethyl)-carbamic acid benzyl ester bisulfite adduct 3 useful for preparing compound 1. As described in Preparation 1, the bisulfite adduct 3 can be prepared by reductive amination of cyclohexanecarboxaldehyde by 2,2-diethoxyethylamine using sodium triacetoxyborohydride, followed by addition of an amino-protecting group, deprotection of the aldehyde functionality, and conversion to the bisulfite adduct by reaction with sodium bisulfite. Alternatively, the initial reductive amination can be performed by catalytic hydrogenation. Suitable hydrogenation catalysts, include, but are not limited to, palladium, platinum, and Raney nickel catalysts.

Pharmaceutical Compositions

The crystalline sulfate salt forms of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a crystalline sulfate salt of compound 1 or a solvate thereof. Optionally, such pharmaceutical compositions may contain other therapeutic and/or formulating agents if desired. When discussing compositions, it is understood the term "salt of the invention" includes the crystalline sulfate salt of compound 1 as well as solvates, in particular, the hydrate, thereof.

The pharmaceutical compositions of the invention typically contain a therapeutically effective amount of the active agent, present in the form of a salt of the invention. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The salts of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The salts of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the salts of this invention may be administered in combination with one or more other therapeutic agents. In this embodiment, a salt of this invention is either physically mixed with the other therapeutic agent to form a composition containing both agents; or each agent is present in separate and distinct compositions which are administered to the patient simultaneously or sequentially.

For example, a salt of the invention can be combined with second therapeutic agent using conventional procedures and equipment to form a composition comprising a compound 1 and a second therapeutic agent. Additionally, the therapeutic agents may be combined with a pharmaceutically acceptable carrier to form a pharmaceutical composition comprising a salt of the invention, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the present active agent may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl}amide, or 4-(4-{[(2-isopropyl-1H-benzoimidazole-4-carbonyl)amino]methyl}-piperidin-1- ylmethyl)piperidine-1-carboxylic acid methyl ester may be used as the second therapeutic agent.

Additional useful prokinetic agents include, but are not limited to, 5-HT$_3$ receptor agonists (e.g. pumosetrag), 5-HT$_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic M$_1$ and M$_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the salts of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 μg/day to about 100 mg/day.

Accordingly, the pharmaceutical compositions of the invention optionally include a second therapeutic agent as described above.

The following examples illustrate representative pharmaceutical compositions of the present invention:

Formulation Example A

Hard Gelatin Capsules for Oral Administration

A salt of the invention (50 g), spray-dried lactose (200 g) and magnesium stearate (10 g) are thoroughly blended. The resulting composition is loaded into a hard gelatin capsule (260 mg of composition per capsule).

Formulation Example B

Hard Gelatin Capsules for Oral Administration

A salt of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

Formulation Example C

Gelatin Capsules for Oral Administration

A salt of the invention (10 mg), polyoxyethylene sorbitan monooleate (50 mg), and starch powder (250 mg) are thoroughly blended and then loaded into a gelatin capsule (310 mg of composition per capsule).

Formulation Example D

Tablets for Oral Administration

A salt of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

Formulation Example E

Tablets for Oral Administration

A salt of the invention (25 mg), microcrystalline cellulose (400 mg), fumed silicon dioxide (10 mg), and stearic acid (5 mg) are thoroughly blended and then compressed to form tablets (440 mg of composition per tablet).

Formulation Example F

Single-Scored Tablets for Oral Administration

A salt of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

Formulation Example G

Suspension for Oral Administration

The following ingredients are thoroughly mixed to form a suspension for oral administration containing 100 mg of active ingredient per 10 mL of suspension:

| Ingredients | Amount |
| --- | --- |
| Salt of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Formulation Example H

Dry Powder Composition

A micronized salt of the invention (1 mg) is blended with lactose (25 mg) and then loaded into a gelatin inhalation cartridge. The contents of the cartridge are administered using a powder inhaler.

Formulation Example J

Injectable Formulation

A salt of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of salt of the invention, (i.e. crystalline salt, or solvate) that is suitable for the particular mode of administration, can be used in the pharmaceutical compositions discussed above.

Utility

The present active agent, 3-endo-(8-{2-[cyclohexylmethyl-((S)-2,3-dihydroxy-propionyl)amino]ethyl}-8-aza-bicyclo[3.2.1]oct-3-yl)benzamide sulfate, is an antagonist at the mu opioid receptor and therefore the salts of the invention are expected to be useful for treating medical conditions mediated by mu opioid receptors or associated with mu opioid receptor activity, i.e. medical conditions which are ameliorated by treatment with a mu opioid receptor antagonist. In particular, the salts of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The present salt forms are also expected to be useful for treating post-operative ileus, a disorder of reduced motility of the gastrointestinal tract that occurs after abdominal or other surgery. In addition, it has been suggested that mu opioid receptor antagonist compounds, such as compound 1 may be used for reversing opioid-induced nausea and vomiting.

Since compound 1 has been shown to increase motility of the gastrointestinal (GI) tract in animal models, the salts of the invention are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a salt of the invention.

When used to treat disorders of reduced motility of the GI tract or other conditions mediated by mu opioid receptors, the salts of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

The present active agent is optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

As described above, salts of the invention are mu opioid receptor antagonists. The invention further provides, therefore, a method of antagonizing a mu opioid receptor in a mammal, the method comprising administering a salt of the invention to the mammal.

Among other properties, the present active agent in freebase and sulfate salt form has been found to exhibit potent binding to mu opioid receptors and little or no agonism in mu receptor functional assays. Therefore, the salts of the invention are potent mu opioid receptor antagonists. Further, active agent has demonstrated predominantly peripheral activity as compared with central nervous system activity in animal models. Therefore, the salts of the invention can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

DIPEA=N,N-diisopropylethylamine
DMF=N,N-dimethylformamide
EtOAc=ethyl acetate
EtOH=ethanol
MeTHF=2-methyltetrahydrofuran
MTBE=tert-butyl methyl ether
NaHMDS=sodium bis(trimethylsilyl)amide
PyBop=benzotriazol-1-yloxytripyrrolidino-phosphonium hexafluorophosphate
psi=pounds per square inch
Rt=retention time
THF=tetrahydrofuran Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Endo/exo ratios of products were determined by HPLC analysis using the protocols described below. Reaction mixtures were worked up as described specifically in each reaction; commonly they were purified by extraction and other purification methods such as temperature-, and solvent-dependent crystallization, and precipitation. Characterization of reaction products was routinely carried out by mass and $^1$H-NMR spectrometry. For NMR measurement, samples were dissolved in deuterated solvent ($CD_3OD$, $CDCl_3$, or $DMSO-d_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.
General HPLC Conditions
 Column: Zorbax SB-Aq, 5 µm. 4.6×250 mm
 Column temperature: 40° C.
 Flow rate: 1.0 mL/min
 Mobile Phases: A=Water/ACN (98:2)+0.1% TFA
  B=Water/ACN (10:90)+0.1% TFA,
 Injection volume: 10 µL
 Detector wavelength: 214 nm
HPLC Method 1
 Crude compounds were dissolved in Water/ACN (50:50) at about 1 mg/mL and analyzed using the following gradient over 20 min (time (min)/% B): 0/10, 2.5/20, 9/75, 15/90, 17/90, 18/10, 20/10.
HPLC Method 2
 Compounds were dissolved in Water/ACN (90:10) at about 1 mg/mL and analyzed using the following gradient over 30 min (time (min)/% B): 0/10, 13/10, 23/65, 28/90, 29/90, 30/10.
HPLC Method 3
 Compounds were dissolved in Water/ACN (90:10) at about 1 mg/mL and analyzed using the following gradient over 55 min (time (min)/% B): 0/10, 10/20, 46/75, 47/90, 50/10, 55/10.

Preparation 1

Synthesis of
N-cyclohexylmethyl-(2-oxoethyl)-carbamic acid benzyl ester bisulfite adduct a. Preparation of
N-cyclohexylmethyl-(2,2-diethoxyethyl)amine To a mixture of 2,2-diethoxyethylamine (209 mL, 1.43 mol) and MeTHF (1050 L) was added cyclohexanecarbaldehyde (107 mL, 0.89 mol). The reaction mixture was stirred for 30 min at room temperature and cooled to 0° C. Sodium triacetoxyborohydride (378 g, 1.79 mol) was added over 40 min and the reaction mixture was stirred for 2 h and cooled to 0° C. 1 M NaOH (1 L) was added. The organic layer was washed with brine in water (1:1, 2×1 L) and the volume was reduced to ~20%. MeTHF (1 L) was added and the volume reduced to ~20%. The solution of the crude title intermediate was used directly in the next step.

b. Preparation of
N-cyclohexylmethyl-(2,2-diethoxyethyl)carbamic acid benzyl ester To the product of the previous step (~213 g, ~0.9 mol) was added MeTHF (2 L) and DIPEA (233 mL, 1.34 mol). The reaction mixture was cooled to 0° C. and benzylchloroformate (140 mL, 0.98 mol) was added dropwise. The reaction mixture was stirred for 30 min at 0° C., for 2 h at 0° C. to room temperature, and then for 1 h at room temperature. Water (1.6 L) was added and the reaction mixture was stirred for 10 min. The phases were separated and the organic layer was washed with sodium bicarbonate (1.6 L) and water (1.6 L). The layers were separated and the organic layer was reduced to about 20%. MeTHF (1 L) was added and the volume reduced to ~20%. The solution of the crude title intermediate was used directly in the next step.

c. Synthesis of
N-cyclohexylmethyl-(2-oxoethyl)-carbamic acid benzyl ester bisulfite adduct To the product of the previous step (~302 g, ~0.62 mol) and acetonitrile (2 L) was added 1 M HCl (2 L) and the reaction mixture was stirred at 30° C. for 7 h. Ethyl acetate (2 L) was added and the reaction mixture was stirred for 10 min. The phases were separated, the organic layer was washed with 1 M HCl (1.5 L), the phases were again separated and the organic layer was washed with 0.5 M HCl (1 L). Sodium bisulfite (71.4 g, 0.69 mol) was added and the reaction mixture was stirred overnight, and then filtered. The reactor and filter cake were washed with ethyl acetate (1 L). The resulting solution was dried in air for 2 h and under vacuum overnight to provide the title compound as a white solid (199 g, >99% area purity by HPLC). The filtrate was treated by the same procedure to provide a second lot of the title compound (30 g).

Preparation 2

Synthesis of
3-endo-(8-azabicyclo[3.2.1]oct-3-yl)-benzamide a. Preparation of 8-benzyl-3-exo-(3-methoxyphenyl)-8-azabicyclo[3.2.1]octan-3-ol To a 3 L flask was added cerous chloride powder (194 g, 0.79 mol). The flask was flushed with nitrogen and THF (800 mL) was added. The reaction mixture was stirred at 25° C. for 1 h. To the mixture was added ~1M 3-methoxyphenyl magnesium bromide in THF (800 mL, 0.87 mol) dropwise. The resulting slurry was stirred at 3° C. for 1.5 hours. A solution of 8-benzyl-8-aza-bicyclo[3.2.1]octan-3-one (120.4 g, 0.56 mol) in THF (200 mL) was then added dropwise, while maintaining the internal temperature at −5° C. The resulting solution was stirred for 15 min. The reaction mixture was added to a flask containing 6 N HCl (800 mL) maintaining the temperature at 10° C. After solvent was removed by rotary evaporation, the reaction mixture was stirred at room temperature overnight. The solids were isolated by filtration, washed with 6N HCL (70 mL) and acetonitrile (3×70 mL), and dried to provide the HCl salt of the title intermediate as an off-white solid (161 g).

b. Preparation of 8-benzyl-3-(3-methoxyphenyl)-8-azabicyclo[3.2.1]oct-2-ene

To a 3 L flask was added 8-benzyl-3-exo-(3-methoxyphenyl)-8-azabicyclo[3.2.1]octan-3-ol hydrochloride (383.9 g, 1.06 mol), 6 M HCl (800 mL), and MeTHF (200 mL). The resulting slurry was heated at 70° C. for 2.5 h under nitrogen. The reaction mixture was transferred to a 12 L reactor and cooled to 10° C. The reaction flask was washed with MeTHF (1 L) that was added to the 12 L reactor. NaOH (50 wt % in water, 200 mL) was added and additional NaOH (50 wt %, 150 mL) was added in portions until pH ~13 was reached. The phases were separated, the water layer was extracted with MeTHF (1 L), and combined MeTHF layers were washed with brine (1 L). Solvent was reduced by rotary evaporation at 30 to 40° C. yielding the title intermediate (360 g) as a thick oil. EtOH (1.5 L) was added and the volume was reduced to ~500 mL and then adjusted to 1.8 L.

c. Preparation of 3-endo-(3-methoxyphenyl)-8-azabicyclo[3.2.1]octane

To 8-benzyl-3-(3-methoxyphenyl)-8-azabicyclo[3.2.1]oct-2-ene (in EtOH 95%, 400 mL, 0.20 mol), prepared in the previous step, was added 6 M HCl (45 mL) and then MeTHF (50 mL). The reaction mixture was purged with nitrogen, heated to 40° C. and palladium on carbon (10 weight %, 8 g) was added. The reactor was pressurized with hydrogen (3×20 psi) and then hydrogenated at 20 psi at 40° C. for 18 h. The reaction mixture was filtered through Celite, concentrated, washed with MeTHF (2×100 mL), filtered through a coarse glass filter, washed with MeTHF (10 mL) and dried on the filter to provide the HCl salt of the title intermediate as white solid (31 g, single isomer, (exo isomer undetectable by HPLC)). An additional 5.2 g of product was recovered from the mother liquor.

d. Preparation of 3-endo-(8-azabicyclo[3.2.1]oct-3-yl)-phenol

To a 500 mL flask was added 3-endo-(3-methoxyphenyl)-8-azabicyclo[3.2.1]octane hydrochloride (115 g, 0.45 mol) and hydrobromic acid (48 weight % in water, 100 mL, 0.88 mol). The mixture was heated to 120° C. and held at that temperature for 24 h with stirring. Additional hydrobromic acid solution (25 mL) was added and the reaction mixture was heated with stirring for 6 h and then cooled to 70° C. Acetonitrile (200 mL) was added and the resulting slurry was cooled to 10° C. and then filtered, and the filter cake was washed with acetonitrile (50 mL) to yield the HBr salt of the title intermediate (99 g, >99% pure) as a white granular solid.

e. Preparation of 2,2,2-trifluoro-1-[3-endo-(3-hydroxyphenyl)-8-azabicyclo[3.2.1]oct-8-yl]ethanone To a solution of 3-endo-(8-azabicyclo[3.2.1]oct-3-yl)-phenol hydrobromide (54.4 g, 0.19 mol), toluene (210 mL), and triethylamine (40 mL, 0.29 mol), was added trifluoroacetic anhydride (54 mL, 0.38 mol) over 20 min. The reaction mixture was stirred at 40° C. for 2 h. Ethyl acetate (370 mL) and brine in water (1:1, 265 mL) were added. The reaction mixture was stirred for 15 min, the phases were separated. To the organic layer was added saturated sodium bicarbonate (300 mL) and the mixture was stirred vigorously overnight. The phases were separated and the organic layer was washed with brine in water (1:1, 265 mL) dried over sodium sulfate and most of the solvent was removed by rotary evaporation. Toluene (100 mL) was added and the solvent removed by rotary evaporation to provide the crude title intermediate.

f. Preparation of trifluoromethanesulfonic acid 3-endo-[8-(2,2,2-trifluoro-acetyl)-8-azabicyclo[3.2.1]oct-3-yl]phenyl ester To a 500 mL flask was added the ethyl acetate solution (220 mL) of the intermediate of the previous step (32.8 g, 0.11 mol) and triethylamine (23 mL. 0.17 mol). The solution was cooled to 5° C. and trifluoromethane sulfonyl chloride (14 mL, 0.13 mol) was added dropwise. The mixture was allowed to warm to 25° C. and stirred at that temperature for 1 h. Saturated sodium bicarbonate (200 mL) was added, the layers were separated, brine (150 mL) was added to the organic layer, the layers were again separated, and solvent was removed from the organic layer to provide the crude title intermediate.

g. Preparation of 3-endo-[8-(2,2,2-trifluoroacetyl)-8-azabicyclo[3.2.1]oct-3-yl]-benzonitrile To a 100 mL flask was added trifluoromethanesulfonic acid 3-endo-[8-(2,2,2-trifluoro-acetyl)-8-azabicyclo[3.2.1]oct-3-yl]phenyl ester (25.3 g, 58.7 mmol), tris(dibenzylideneacetone)dipalladium (0) (0.81 g, 0.9 mmol), 1,1'-bis(diphenylphosphino)ferrocene (1.01 g, 1.8 mmol), and zinc cyanide (4.2 g, 35.8 mmol). Three times, the flask was purged with nitrogen for 5 min and then placed under house vacuum for 5 min. To the flask was added DMF (150 mL) and distilled water (2.5 mL). The solution was purged with nitrogen with stirring for 10 min, heated to 120° C. and stirred at 120° C. under nitrogen for 4 h. When the reaction was completed 20 g of product from a previous lot, prepared by the same procedure, was added and stirred for 20 min.

Most of the solvent was removed by distillation and the solution was cooled to 22° C. To the solution was added ethyl acetate (445 mL) and the resulting solution was filtered through Celite. Sodium bicarbonate (450 mL) was added and the solution was stirred for 15 min. The layers were separated and the organic layer was washed with diluted brine (2×95 mL), and filtered through sodium sulfate. The volume was reduced to about 50 mL by removal of ethyl acetate. Isopropyl alcohol (150 mL) was added and the solution was agitated at 22° C. for 1 h. Solids were isolated by filtration and washed with isopropyl alcohol (2×25 mL) to provide the title intermediate (33.5 g, 100% pure by HPLC) as an off-white/light brown solid. A second crop of product (6.3 g, >98% pure by HPLC) was isolated from the filtrate.

h. Synthesis of 3-endo-(8-azabicyclo[3.2.1]oct-3-yl)-benzamide

A solution of 3-endo-[8-(2,2,2-trifluoroacetyl)-8-azabicyclo[3.2.1]oct-3-yl]-benzonitrile (10 g, 32 mmol) in sulfuric acid (96%, 12 mL) was heated to 50° C. with stirring and held at that temperature with stirring for 2 h. The reaction mixture was cooled to 22° C. and added slowly to a 500 mL flask containing 5 N NaOH (90 mL) and methanol (100 mL) which was cooled to 10° C. Salt precipitates were filtered and the filtrate was stirred at 22° C. for 1 h. The reaction mixture was concentrated under reduced pressure. To the residue was added MeTHF (150 mL) and the reaction mixture was stirred at 22° C. for 5 min. The layers were separated and MeTHF (100 mL) was added to the aqueous layer. The layers were separated and brine (150 mL) was added to the combined organic layers. The layers were separated and the organic layer was dried over potassium carbonate and filtered, and the solvent was removed. A mixture of EtOH (25 mL) and concentrated HCl (2.6 mL) was added to the residue with stirring and then MTBE (25 mL) was added and the solution was stirred at 22° C. Precipitated solids were filtered and air dried to provide the HCl salt of the title compound (8 g, 97% purity by HPLC) as a white solid.

Preparation 3

Synthesis of 3-endo-(8-azabicyclo[3.2.1]oct-3-yl)benzamide a. Preparation of trifluoro-methanesulfonic acid 8-benzyl-8-azabicyclo[3.2.1]oct-2-en-3-yl ester To a 500 mL flask was added 8-benzyl-8-azabicyclo[3.2.1]octan-3-one hydrochloride (50.4 g, 200 mmol), EtOAc (160 mL), and 4 N NaOH (50 mL). The reaction mixture was heated to 30° C. and stirred at that temperature for 1 h. The layers were separated and the aqueous layer was discarded. The volume of the organic layer was reduced to ~40 mL by rotary evaporation and THF (270 mL) was added.

The resulting solution was added to a 1 L flask and cooled to −20° C. A NaHMDS solution (1 M in THF, 230 mL, 230 mmol) was added to the flask over 15 min. The reaction mixture was stirred at −20±5° C. for 1 h. N-phenyl-bis(trifluoromethanesulfonimide (82.2 g, 230 mmol) was added to the reaction mixture in portions over 5 min and the mixture was stirred at −20° C. to −10° C. for 1 h. To the reaction mixture was added 1 N NaOH (200 mL) and the mixture was allowed to warm to 22° C. with stirring. Solvent was partially removed by rotary evaporation at 30° C. to a volume of 450 mL. To the remaining reaction mixture was added EtOAc (300 mL) and heptane (150 mL). The mixture was stirred at 22° C. for 5 min. The layers were separated and the aqueous layer was discarded. The organic layer was washed with 1N NaOH (3×450 mL). The aqueous layers were discarded. The organic layer was concentrated by rotary evaporation to provide the title intermediate (77 g, >96% purity by HPLC method 1).

$^1$H NMR (d$_6$-DMSO, 400 MHz): δ (ppm) 7.25-7.35 (m, 5H), 6.05 (d, J=5.2, 1H), 3.64 (q, J=13.2, 2H), 3.40-3.44 (m, 2H), 2.77 (d, J=16.4, 1H), 1.79-2.09 (m, 5H), 1.52-1.59 (m, 1H).

b. Preparation of 3-(8-benzyl-8-azabicyclo[3.2.1]oct-2-en-3-yl)benzamide

To the crude product of the previous step was added THF (420 mL) and the solution was purged with nitrogen for 5 min. To a 2 L flask was added 3-carbamoylphenyl boronic acid (98%, 33.0 g, 200 mmol), palladium (II) acetate (98%. 0.46 g, 2 mmol), 1,1'-bis(diphenylphosphino)ferrocene (97%, 1.1 g, 2 mmol). and potassium fluoride (34.9 g, 600 mmol) followed by the THF solution of trifluoro-methanesulfonic acid 8-benzyl-8-aza-\bicyclo[3.2.1]oct-2-en-3-yl ester. The resulting mixture was purged with nitrogen for 5 min, heated to reflux (67° C.) under nitrogen and stirred for 2 h. The reaction mixture was cooled to 30° C., then EtOAc (500 mL) and 1 N NaOH (500 mL) were added and the mixture was stirred at 22° C. for 10 min. The layers were separated and the aqueous layer was discarded. The organic layer was washed with a mixture of brine (250 mL) and water (250 mL) and stirred for 5 min. The layers were separated and the aqueous layer was discarded. The organic layer was briefly dried over Na$_2$SO$_4$, filtered, and solvent was partially removed. Product precipitated as light yellow solids during solvent removal. The resulting slurry (about 200 mL) was filtered and the solids were washed with cold EtOAc (0° C., 100 mL) and dried under high vacuum at 25° C. to provide the title intermediate (42.5 g) as a light yellow solid.

The mother liquor and the above washes were combined and concentrated and the resulting slurry (about 100 mL) was stirred at 5° C. for 30 min and filtered. The filtered solids were washed with cold EtOAc (0° C., 30 mL) and dried under high vacuum to provide a second crop of the title intermediate (7 g, combined yield 78%, >98.5% pure by HPLC method 1).

(m/z): [M+H]$^+$ calcd for C$_{21}$H$_{22}$N$_2$O, 319.18; found 319.4.
$^1$H NMR (CDCl$_3$, 400 MHz): δ (ppm) 7.9 (s, 1H), 7.63 (d, J=6.4, 1H), 7.57 (d, J=6.4, 1H), 7.21-7.42 (m, 6H), 6.38 (d, J=4.4, 1H), 6.13 (s, br, 1H), 5.83 (s, br, 1H), 3.68-3.76 (m, 2H), 3.46-3.51 (m, 2H), 2.92 (d, J=17.2, 1H), 2.18-2.26 (m, 1H), 2.04-2.12 (m, 2H), 1.86-1.92 (m, 1H), 1.58-1.65 (m, 1H).

c. Synthesis of 3-endo-(8-azabicyclo[3.2.1]oct-3-yl)benzamide

To a 1 L hydrogenation vessel was added 3-(8-benzyl-8-azabicyclo[3.2.1]oct-2-en-3-yl)benzamide (40 g, 125 mmol), EtOH (800 mL), 6 M HCl (42 mL) and water (80 mL) and the mixture was stirred at 22° C. until complete dissolution was observed. The reaction mixture was purged with nitrogen for 5 min while being heated to 30° C. over 5 min. To the mixture was added 10 wt % Pd/C (50% in water, 4 g). The mixture was purged at atmospheric pressure with hydrogen for 5-10 min while being heated. The mixture was stirred at 50° C. under a flow of hydrogen at <5 psi (<0.34 atmospheres) for 5 h, resulting in >99% conversion of the reactants, according to HPLC analysis. The solution was cooled to 30° C. and filtered through Celite to provide a solution of the crude HCl salt of the title compound with an endo:exo ratio of ~93:7 by HPLC method 2 endo Rt=10.97, exo Rt=12.67. (m/z): [M+H]$^+$ calcd for C$_{14}$H$_{18}$N$_2$O, 231.15; found 231.2.

Water was removed from the crude product by azeotropic distillation at 30° C. in EtOH (~80 mL) to provide a slurry that was heated to 60° C. until complete dissolution. The solution was cooled to 35° C. and seed crystals of the product (0.05 g) were added. (The seed crystals were prepared according to the process described in Preparation 2.) The resulting slurry was stirred at 22° C. for 30 min, MTBE (120 mL) was added slowly, and the slurry was stirred at 22° C. for 4 h and then at 0° C. for 1 h. The resulting solids were filtered, washed with cold EtOH and dried under high vacuum to provide the HCl salt of the title compound (24.5 g) as a white powder (75% yield, >98.5% purity<0.4% exo isomer by HPLC method 3, endo Rt=8.67, exo Rt=9.43).

(m/z): [M+H]$^+$ calcd for C$_{14}$H$_{18}$N$_2$O 231.15; found 231.2.
$^1$H NMR (d$_6$-DMSO, 400 MHz): δ (ppm) 9.13 (s, br, 1H), 9.03 (s, br, 1H), 8.05 (s, 1H), 7.93 (s, 1H), 7.73 (d, J=7.6, 1H), 7.58 (d, J=7.6, 1H), 7.40 (t, J=7.6, 2H), 3.97 (s, 2H), 3.17-3.23 (m, 1H), 2.39-2.46 (m, 2H), 2.19-2.24 (m, 2H), 1.86-1.89 (m, 2H), 1.59-1.63 (m, 2H).

Example 1A

Synthesis of crystalline 3-endo-(8-{2-[cyclohexylm-ethyl-((S)-2,3-dihydroxy-propionyl)amino]ethyl}-8-aza-bicyclo[3.2.1]oct-3-yl)benzamide sulfate a. Preparation of N-cyclohexylmethyl-(2-oxoethyl)-carbamic acid benzyl ester To a 100 mL flask was added N-cyclohexylmethyl-(2-oxoethyl)-carbamic acid benzyl ester bisulfite adduct (3.94 g, 1 mmol) and MeTHF (35 mL), followed by water (25 mL). The resulting slurry was stirred at room temperature for 5 min and 1 M NaOH (8 mL) was added. The reaction mixture was stirred at room temperature for 45 min. The layers were separated and the volume of the organic layer was reduced to ~8 mL to provide the crude title intermediate.

b. Preparation of 2-[3-endo-(3-carbamoylphenyl)-8-azabicyclo[3.2.1]oct-8-yl]-ethyl}cyclohexylmethyl-carbamic acid benzyl ester To the product of the previous step was added DMF (15 mL) followed by 3-endo-(8-azabicyclo[3.2.1]oct-3-yl)-benzamide hydrochloride (2.67 g, 1 mmol) and then DMF (10 mL). The mixture was stirred at room temperature for 30 min, cooled to 10° C. and then sodium triacetoxyborohydride (4.25 g, 2 mmol) was added. The reaction mixture was stirred at room temperature for 90 min and then cooled to 10° C. Isopropyl acetate (100 mL) was added, followed by 1 M NaOH (50 mL). The mixture was stirred for 15 min, and the phases were separated. The organic layer was washed with brine in water (1:1, 2×50 mL) and the volume of the organic layer was reduced to ~10 mL to provide the crude title intermediate.

c. Preparation of 3-endo-{8-[2-(cyclohexylmethyl-amino)ethyl]-8-aza-bicyclo[3.2.1]oct-3-yl}benzamide To the product of the previous step was added EtOH (30 mL) and concentrated HCl (1.5 mL). The solution was purged with nitrogen, 10% palladium on carbon (470 mg) was added and the mixture was purged with nitrogen for 5 min and then hydrogenated at 30 psi overnight. After purging with nitrogen for 2 min, the solution was filtered through Celite and solvent was removed to ~10 mL. Isopropyl acetate (40 mL) and 1 M NaOH (20 mL) were added. The layers were separated and the organic layer was washed with brine (20 mL), phases were separated and organic solvent removed to 5-10 mL. Isopropyl acetate (20 mL) was added and the volume reduced to ~8 mL to which isopropyl acetate (20 mL) was added. The resulting slurry was stirred at room temperature for 2 h. The product was isolated by filtration, the reaction flask and filter cake were washed with isopropyl acetate (10 mL) to yield the title intermediate (2.4 g, 98% pure) as an off-white solid.

d. Preparation of 3-endo-(8-{2-[cyclohexylmethyl-((S)-2,3-dihydroxy-propionyl)amino]ethyl}-8-aza-bicyclo[3.2.1]oct-3-yl)benzamide sulfate (hydrate form)

To a 500 mL flask was added 3-endo-{8-[2-(cyclohexylm-ethylamino)ethyl]-8-aza-bicyclo[3.2.1]oct-3-yl}benzamide (31 g, 83.9 mmol) and DMF (150 mL). The mixture was stirred for 10 min and then benzotriazol-1-yloxytris(pyrrolidino)-phosphonium hexafluoro-phosphate (56.8 g, 109 mmol) and lithium (4S)-2,2-dimethyl-1,3-dioxolane-4-carboxylate (15.6 g, 92.3 mmol) were added and the mixture was stirred at room temperature for 2 h. Ethyl acetate (600 mL) and 0.5 M NaOH (300 mL) were added and the phases were separated. The organic layer contained crude (S)-2,2-dim-ethyl-[1,3]dioxolane-4-carboxylic acid {2-[3-(3-carbamoyl-phenyl)-8-azabicyclo[3.2.1]oct-8-yl]ethyl}cyclohexylmethyl-amide (~84 mmol) which was not isolated.

The organic layer was washed with brine in water (1:1, 2×300 mL) and the phases were separated. To the organic layer was added 2 M $H_2SO_4$ (42 mL) and the reaction mixture was stirred at room temperature overnight. Acetonitrile (300 mL) was added and the resulting slurry was stirred for 2 h. The product was isolated by filtration, the filter cake was washed with acetonitrile (200 mL), dried in air for 2 h and then under vacuum at room temperature for 20 h to provide the title compound (40 g, 97% pure by HPLC) as a white powder.

e. Synthesis of crystalline 3-endo-(8-{2-[cyclohexyl-methyl-((S)-2,3-dihydroxy-propionyl)amino]ethyl}-8-aza-bicyclo[3.2.1]oct-3-yl)benzamide sulfate To a 100 mL flask was added 3-endo-(8-{2-[cyclohexylm-ethyl-((S)-2,3-dihydroxy-propionyl)amino]ethyl}-8-aza-bi-cyclo[3.2.1]oct-3-yl)benzamide sulfate hydrate form (2 g) and MeOH (40 mL). The resulting slurry was heated to 65° C. under nitrogen for 20 min resulting in complete dissolution. The solution was cooled to room temperature with stirring. About 20 mL of solvent was removed under slightly reduced pressure and the resulting slurry stirred at room temperature overnight. The product was isolated by filtration, and the flask and filter cake were washed with acetonitrile (2×5 mL). The filter cake was dried in air for 2 h and then under vacuum at room temperature overnight to provide the title compound (1.71 g, >99% pure by HPLC, ~85% yield) as a white powder.

A sample prepared according to the above procedure was characterized by $^1$H NMR (400 MHz, DMSO $d_6$): δ (ppm) 9.08 & 8.94 (two sets of brs, 1H), 7.99-8.04 (m, 2H), 7.74-7.76 (m, 1H), 7.68-7.70 (m, 1H), 7.41-7.45 (m, 2H), 4.81, 5.00 and 5.30 (three sets of brs, 2H), 4.34 (deformed m, 1H), 4.00 & 4.05 (deformed m, 2H), 3.01-3.25 and 3.47-3.55 and 3.75-3.82 (three sets of m, 10H), 2.50-2.55 (m, 2H), 1.99 (deformed m, 2H), 1.56-1.70 (m, 8H), 1.15-1.19 (m, 3H), 0.89-0.99 (m, 2H).

Example 1B

Synthesis of crystalline 3-endo-(8-{2-[cyclohexylm-ethyl-((S)-2,3-dihydroxy-propionyl)amino]ethyl}-8-aza-bicyclo[3.2.1]oct-3-yl)benzamide sulfate a. Preparation of 3-endo-(8-{2-[cyclohexylmethyl-((S)-2,3-dihydroxy-propionyl)amino]ethyl}-8-aza-bicyclo[3.2.1]oct-3-ylbenzamide sulfate A mixture of 3-endo-{8-[2-(cyclohexylmethylamino) ethyl]-8-aza-bicyclo[3.2.1]oct-3-yl}benzamide (100 g, 270.6 mmol) and DMF (480 mL) was stirred for 10 min and then cooled at 0° C. Benzotriazol-1-yloxytris(pyrrolidino) phosphonium hexafluorophosphate (183 g, 352 mmol) and lithium (4S)-2,2-dimethyl-1,3-dioxolane-4-carboxylate (49.3 g, 324 mmol) were added in one portion at 0° C. The reaction mixture was stirred at room temperature for 6 h. Isopropyl acetate (2.0 L) and 1 M NaOH (1.0 L) were added, the reaction mixture was stirred for 15 min, and the phases were separated. The organic layer was washed with brine in water (1:1, 2×1.0 L) and the phases were separated. The organic layer was reduced to a quarter of the volume (~500 mL), acetonitrile (500 mL) was added and the reaction mixture was stirred until homogenous to provide a solution of intermediate (S)-2,2-dimethyl-1,3-dioxolane-4-carboxylic acid 2-[3-endo-(3-carbamoyl-phenyl)-8-azabicyclo[3.2.1] oct-8-yl]-ethyl-cyclohexylmethyl-amide in isopropyl acetate and acetonitrile.

An aliquot of the above solution of intermediate (3.03 g, 6.09 mmol) in isopropyl acetate/acetonitrile (22.5 mL) was combined with 2.0 M sulfuric acid in water (3.68 mL) and held at 25° C. for 20 h and then held at 10° C. with stirring for 5 h. The reaction solution was filtered, and the filter cake was washed with acetonitrile (25 mL) and dried to yield the interb. Synthesis of crystalline 3-endo-(8-{2-[cyclohexyl-methyl-((S)-2,3-dihydroxy-propionyl)amino]ethyl}-8-aza-bicyclo[3.2.1]oct-3-yl)benzamide sulfate A mixture of 3-endo-(8-2-[cyclohexylmethyl-((S)-2,3-dihydroxy-propionyl)-amino]-ethyl-8-aza-bicyclo[3.2.1]oct-3-yl)-benzamide sulfate intermediate grade (154.0 g, 277.1 mmol) prepared as in the previous step and methanol/10% water (616 mL) was heated at 65° C. over 45 min with stirring. The reaction mixture was cooled to 55° C., seed crystals of the title product (120 mg) were added, the reaction mixture was stirred at 55° C. for 1 h, and the temperature was reduced to 20° C. at the rate of 10° C./h and then held for 8 h. The reaction mixture was cooled to 5° C., held for 30 min, and filtered. The filter cake was washed with methanol (2×25 mL) and dried overnight under high vacuum to yield the title compound (126.3 g, 99.9% purity)

Example 2

Recrystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate (hydrate form)

Compound 1 sulfate (hydrate form) (920 mg) was suspended in acetonitrile (5 mL) and heated to 65° C. Water (2.4 mL) was then added dropwise until complete dissolution was achieved. The resulting solution was cooled to ambient temperature over 20 min. Nucleation was observed around 35° C. The solids were isolated by vacuum filtration, washed with acetonitrile (5 mL) and dried to provide the title compound.

Example 3

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate Compound 1 sulfate (hydrate form) (50 mg) was dispersed in a water (10%) and methanol (90%) solvent mixture (0.83 mL) and heated to 60° C. with stirring. The resulting solution was allowed to cool to ambient temperature over 2 h. The resulting solids were isolated by vacuum filtration to provide the title compound (8 mg).

Example 4

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate Compound 1 sulfate (hydrate form) (42 mg) was dispersed in a water (25%) and methanol (75%) solvent mixture (0.42 mL) and heated to 60° C. with stirring. The resulting solution was allowed to cool to ambient temperature. The volume was reduced by 50% by rotary evaporation and the solution was left at ambient temperature overnight. The resulting solids were isolated by vacuum filtration to provide the title compound (8 mg).

Example 5

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate Compound 1 (11 mg) was dissolved in a toluene (22%) and acetonitrile (78%) solvent mixture (0.2 mL). Acetonitrile (0.15 mL) was added, followed by 0.04 M sulfuric acid in acetonitrile (0.59 mL). A solid precipitate formed on addition of acid. The reaction mixture was left at ambient temperature for 12 h. The resulting solids were isolated by filtration to provide the title compound.

Example 6

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate Compound 1 (38 mg) was dissolved in dichloromethane (0.5 mL). To the solution was added 0.04 M sulfuric acid in acetonitrile (1.91 mL). A solid precipitate formed on addition of acid. The reaction mixture was left at ambient temperature for 12 h. The resulting solids were isolated by filtration to provide the title compound.

Example 7

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate Compound 1 (22 mg) was dissolved in a toluene (23%) and acetonitrile (77%) solvent mixture (0.41 mL). To the solution was added 0.04 M sulfuric acid in acetonitrile (1.20 mL). A solid precipitate formed on addition of acid. Water (0.16 mL) was added to the reaction mixture dissolving the precipitate. Nucleation was observed after 2 h. The resulting solids were isolated by vacuum filtration to provide the title compound.

Example 8

Crystallization of 3-endo-(8-{2-[cyclohexylmethyl-((S)-2,3-dihydroxy-propionyl)amino]ethyl}-8-aza-bicyclo[3.2.1]oct-3-yl)benzamide sulfate (hydrate form)

Crystalline compound 1 sulfate (7.1 g) was dissolved in a solvent mixture of water (42 mL) and acetonitrile (25 mL). The solution was lyophilized to produce an amorphous sulfate salt. The amorphous salt (6.6 g) was dispersed in a acetonitrile (75%) and water (25%) solvent mixture (34.6 mL) and heated to 65° C. for 10 min with stirring and allowed to cool with stirring until ambient temperature was reached. After 12 h, the resulting solids were isolated by vacuum filtration to provide the title compound (5.4 g).

Examples 9-17

Properties of Salt Forms of the Invention

Samples of the crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide (compound 1) prepared as in Example 1A and of the crystalline hydrate of the sulfate salt of compound 1, prepared as in Example 2 were analyzed by x-ray powder diffraction (XRPD), differential scanning calorimetry (DSC), thermogravimetric analysis (TGA) infrared spectroscopy (IR) and ion chromatography.

Example 10

X-Ray Powder Diffraction

X-ray powder diffraction patterns of FIGS. 1 and 4 were obtained with a Rigaku diffractometer using Cu Kα (30.0 kV, 15.0 mA) radiation. The analysis was performed with the goniometer running in continuous-scan mode of 3° per min with a step size of 0.03° over a range of 2 to 40°. Samples were prepared on quartz specimen holders as a thin layer of powdered material. The instrument was calibrated with a silicon standard.

Example 11

Thermal Analysis

Figure 2:
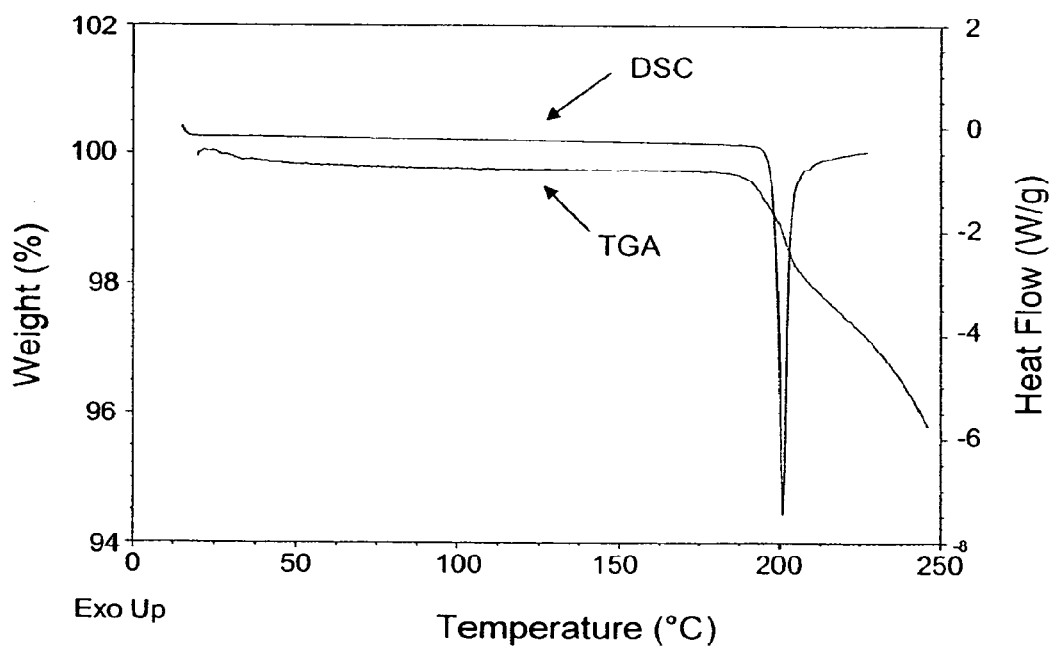
FIG. 2 shows a differential scanning calorimetry (DSC) trace (right side vertical axis) and a thermal gravimetric analysis (TGA) trace (left side vertical axis) for a crystalline sulfate salt of 3-endo-(8-{2-[cyclohexylmethyl-((S)-2,3-dihydroxy-propionyl)amino]ethyl}-8-aza-bicyclo[3.2.1]oct-3-yl)benzamide of the invention.

Differential scanning calorimetry (DSC) was performed using a TA Instruments Model Q-100 module. Data were collected and analyzed using TA Instruments Thermal Advantage for Q Series™ software. A sample of about 1-10 mg was accurately weighed into an aluminum pan with lid. The sample was evaluated using a linear heating ramp of 10° C./min from 5° C. to, typically, 265° C. The DSC cell was purged with dry nitrogen during use. Representative DSC traces for samples of the crystalline sulfate salt and of the crystalline hydrate of a sulfate salt of compound 1 are shown in FIGS. 2 and 5, respectively.

Thermogravimetric analysis (TGA) was performed using a TA Instruments Model Q-500 module. Data were collected and analyzed using TA Instruments Thermal Advantage for Q Series™ software. A sample weighing about 1-5 mg was placed in an aluminum pan on a platinum cradle and scanned from ambient temperature to 300° C. with a linear heating rate of 10° C./min. The balance and furnace chambers were purged with nitrogen during use. Representative TGA traces for samples of a crystalline sulfate salt and of a crystalline hydrate of a sulfate salt of compound 1 are also shown in FIGS. 2 and 5, respectively.

Example 12

Dynamic Moisture Sorption Assessment

Dynamic moisture sorption (DMS) assessment was performed at 25° C. using a VTI atmospheric microbalance, SGA-100 system (VTI Corp., Hialeah, Fla. 33016). A sample size of approximately 5-10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (±5% RH) when the mass of the sample was stable to within 0.02% for 5 consecutive points. Representative DMS traces for samples of a crystalline sulfate salt and of a crystalline hydrate of a sulfate salt of compound 1 are shown in FIGS. 3 and 6, respectively.

Example 13

Infrared Analysis

The infrared (IR) absorption spectrum was determined over the frequency range 4000 to 400 cm$^{-1}$ using an Avatar 360 FT-IR spectrometer equipped with a diffuse reflectance infrared fourier transform spectroscopy (DRIFTS) module. A representative IR absorption spectrum for a sample of a crystalline sulfate salt of the invention had significant absorption bands at 430±1, 590±1, 639±1, 705±1, 867±1, 1036±1, 1053±1, 1105±1, 1171±1, 1231±1, 1277±1, 1375±1, 1391±1, 1452±1, 1476±1, 1553±1, 1596±1, 1639±1, 1664±1, 2852±1, 2907±1, 2928±1, 2967±1, 3168±1, and 3357±1 cm$^{-1}$.

Example 14

X-Ray Diffraction Crystal Structure Analysis

A chunk crystal of the sulfate salt of compound 1 having dimensions of 0.43×0.05×0.031 mm was mounted on a glass fiber. X-ray diffraction crystal structure data was obtained using a Bruker SMART 6K CCD x-ray area detector with window diameter of 13.5 cm, controlled by SMART version 5.630 software (Bruker, 2003) using Cu Kα radiation. The sample to detector distance was 5.039 cm. Data was collected at a temperature of −153±1° C. and was analyzed using SHELXS version 6.14 (Bruker, 2003) software. The following lattice parameters were derived: unit cell is orthorhombic with dimensions a=6.8239 Å, b=16.2275 Å, c=24.2021 Å, α=β=γ=90°; cell volume (V) of 2680.0 Å$^3$; calculated density is 1.38 g/cm$^3$; space group is $P2_12_12_1$(#19) Powder x-ray diffraction peaks predicted from the derived atomic positions according to Mercury 1.4 software were judged by visual inspection to be in excellent agreement with the experimental results of FIG. 1.

Example 15

Solid State Stability Assessment

Samples of the sulfate salt of the invention were stored in multiple open glass vials at 20° C. and 60% relative humidity (RH) and at 40° C. and 75% RH. At specific intervals, the contents of a representative vial was removed and analyzed by DSC, TGA, PXRD, and by HPLC for chemical purity. After 4 weeks of storage, there was no detectable change in the DSC or TGA thermograms nor in the XRPD pattern of samples stored at either condition. The chemical purity of the stored samples by HPLC was unchanged at 99.7%.

Example 16

Determination of Counterion Content

A sample of the sulfate salt of the invention was analyzed by sulfate ion chromatography using a Dionex ICS-2000 ion chromatography system equipped with an anion self-regenerating suppressor, conductivity detector, IonPac AS11-HC analytical anion-exchange column, and IonPac AG11-HC guard column. The sulfate content of the sample was determined to be 17.1% which may be compared with a theoretical sulfate content of 17.6% for one molar equivalent of sulphate ion per mole of parent compound.

Example 17

Determination of Water Content of Hydrate

A sample of the hydrate of the invention was analyzed by TGA coupled with IR analysis of the material vaporized during initial weight loss. The TGA trace shows a weight loss of 3.2% below 100° C. which may be compared with a theoretical weight loss of 3.1% for a monohydrate of compound 1 sulfate. The IR spectrum of the vaporized material was consistent with the reference IR spectrum of water.

Assay 1

Radioligand Binding Assay on Human Mu, Human Delta and Guinea Pig Kappa Opioid Receptors a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin-100 μg/mL streptomycin and 800 μg/mL Geneticin in a 5% $CO_2$, humidified incubator @ 37° C. Receptor expression levels ($B_{max}$ ~2.0 and ~0.414 pmol/mg protein, respectively) were determined using [$^3$H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N'-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 μL containing the appropriate amount of membrane protein (~3, ~2 and ~20 μg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 μM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM naloxone. $K_i$ values for test compounds were calculated, in Prism, from the best fit $IC_{50}$ values, and the $K_d$ value of the radioligand, using the Cheng-Prusoff equation ($K_i = IC_{50}/(1+([L]/K_d))$) where [L]=the concentration of [$^3$H]-Diprenorphine. Results are expressed as the negative decadic logarithm of the $K_i$ values, $pK_i$.

Test compounds having a higher $pK_i$ value in these assays have a higher binding affinity for the mu, delta, or kappa opioid receptor. The sulfate salt of compound 1 exhibited a $pK_i$ value of 9.9 at the human mu opioid receptor.

Assay 2

Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound GTP-Eu present following receptor activation in membranes prepared from CHO-K1 cells expressing the human mu opioid receptor.

a. Mu Opioid Receptor Membrane Preparation

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 pmol/mg protein, respectively. Protein concentration was determined using a Bio-Rad Bradford Protein Assay kit. Membranes were stored in frozen aliquots at −80° C., until required. Lyophilized GTP-Eu and GDP were diluted to 10 μM and 2 mM, respectively, in double distilled $H_2O$ then mixed and permitted to sit at room temperature for 30 minutes prior to transfer to individual aliquots samples for storage at −20° C.

b. Human Mu GTP-Eu Nucleotide Exchange Assay

GTP-Eu nucleotide exchange assays were performed using the DELPHIA GTP-binding kit (Perkin/Elmer) in AcroWell 96 well filter plates according to the manufacturer's specifications. Membranes were prepared as described above, and prior to the start of the assay, aliquots were diluted to a concentration of 200 μg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 μM into Assay Buffer containing 0.1% BSA, and serial (1:5) dilutions then made to generate ten concentrations of compound ranging from 40 pM-80 μM-GDP and GTP-Eu were diluted to 4 μM and 40 nM, respectively, in Assay Buffer. The assay was performed in a total volume of 100 μL containing 5 μg of membrane protein, test compound ranging from 10 pM-20 μM), 1 μM GDP, and 10 nM GTP-Eu diluted in 10 mM $MgCl_2$, 50 mM NaCl, and 0.0125% BSA, (final assay concentrations). A DAMGO (Tyr-D-Ala-Gly-(methyl)Phe-Glyol) concentration-response curve (ranging from 12.8 pM-1 µM) was included on every plate.

Assay plates were prepared immediately prior to assay following the addition of 25 µL of Assay Buffer, 25 µL of test compound, and 25 µL GDP and GTP-Eu. The assay was initiated by the addition of 25 µL membrane protein and allowed to incubate for 30 minutes. The assay plates were then filtered with a Waters vacuum manifold connected to the house vacuum regulated to 10-12 in. Hg and washed with room temperature GTP Wash Solution (2×300 mL). The bottoms of the plates were blotted to remove excess liquid. The plates were then immediately read to determine the amount of bound GTP-Eu by measuring Time Resolved Fluorescence (TRF) on a Packard Fusion Plate ReaderVehicle: DMSO not to exceed 1% final assay concentration.

The amount of bound GTP-Eu is proportional to the degree of activation of the mu opioid receptors by the test compound. The intrinsic activity (IA), expressed as a percentage, was determined as the ratio of the amount of bound GTP-Eu observed for activation by the test compound to the amount observed for activation by DAMGO which is presumed to be a full agonist (IA=100). The sulfate salt of compound 1 demonstrated an intrinsic activity of −5 in this assay. Thus, the present sulfate salt has been shown to be an antagonist.

Assay 3

Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (©1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit $ID_{50}$ values were calculated. Curve minima and maxima were fixed to loperamide control values (indicating 0% reversal) and vehicle controls (indicating 100% reversal), respectively. Results are expressed as $ID_{50}$, the dose required for 50% reversal of the effects of loperamide, in milligrams per kilogram. The sulfate salt of compound 1, administered orally, exhibited an $ID_{50}$ value of 0.26 mg/kg in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A method of treating a mammal having a medical condition ameliorated by treatment with a mu opioid receptor antagonist, wherein the medical condition is opioid-induced bowel dysfunction or post-operative ileus, the method comprising administering to the mammal a therapeutically effective amount of a pharmaceutical composition comprising a pharmaceutically-acceptable carrier and a crystalline salt form which is the hydrate of the sulfate salt of 3-endo-(8-{2-[cyclohexylmethyl-((S)-2,3-dihydroxy-propionyl)amino]ethyl}-8-aza-bicyclo[3.2.1]oct-3-yl)benzamide wherein the crystalline salt form is characterized by an x-ray powder diffraction pattern having two or more diffraction peaks at 2θ values selected from 9.41±0.20, 9.98±0.20, 15.17±0.20, 16.70±0.20, 18.59±0.20, 19.46±0.20, 19.91±0.20, 20.63±0.20, 21.35±0.20, 21.89±0.20, 23.00±0.20, 24.20±0.20, 25.40±0.20, 26.03±0.20, 27.44±0.20, 28.46±0.20, 29.45±0.20, 31.22±0.20, 31.82±0.20, 33.17±0.20, 33.56±0.20, and 36.89±0.20.

2. The method of claim 1 wherein the x-ray powder diffraction pattern comprises two or more diffraction peaks at 2θ values selected from 16.70±0.20, 18.59±0.20, 19.46±0.20, 19.91±0.20, 23.00±0.20, and 24.20±0.20.

3. The method of claim 1, wherein the crystalline salt form is characterized by an x-ray powder diffraction pattern in which the peak positions are substantially in accordance with the peak positions of the pattern shown in FIG. 4.

4. The method of claim 1, wherein the crystalline salt form is characterized by a differential scanning calorimetry trace substantially in accordance with that shown in FIG. 5.

5. The method of claim 1 wherein the medical condition is opioid-induced bowel dysfunction.

6. The method of claim 1 wherein the medical condition is post-operative ileus.

7. A method of reducing a gastrointestinal side effect associated with use of an opioid agent in a mammal, the method comprising administering to the mammal an opioid agent and a crystalline salt form which is the hydrate of the sulfate salt of 3-endo-(8-{2-[cyclohexylmethyl-((S)-2,3-dihydroxy-propionyl)amino]ethyl}-8-aza-bicyclo[3.2.1]oct-3-yl)benzamide wherein the crystalline salt form is characterized by an x-ray powder diffraction pattern having two or more diffraction peaks at 2θ values selected from 9.41±0.20, 9.98±0.20, 15.17±0.20, 16.70±0.20, 18.59±0.20, 19.46±0.20, 19.91±0.20, 20.63±0.20, 21.35±0.20, 21.89±0.20, 23.00±0.20, 24.20±0.20, 25.40±0.20, 26.03±0.20, 27.44±0.20, 28.46±0.20, 29.45±0.20, 31.22±0.20, 31.82±0.20, 33.17±0.20, 33.56±0.20, and 36.89±0.20.

8. The method of claim 7 wherein the x-ray powder diffraction pattern comprises two or more diffraction peaks at 2θ values selected from 16.70±0.20, 18.59±0.20, 19.46±0.20, 19.91±0.20, 23.00±0.20, and 24.20±0.20.

9. The method of claim 7, wherein the crystalline salt form is characterized by an x-ray powder diffraction pattern in which the peak positions are substantially in accordance with the peak positions of the pattern shown in FIG. 4.

10. The method of claim 7, wherein the crystalline salt form is characterized by a differential scanning calorimetry trace substantially in accordance with that shown in FIG. 5.

11. The method of claim 7 wherein the opioid agent is selected from morphine, pethidine, codeine, dihydrocodeine, oxycontin, oxycodone, hydrocodone, sufentanil, fentanyl, remifentanil, buprenorphine, methadone, and heroin.

12. The method of claim 11 wherein the opioid agent is morphine.

13. The method of claim 11 wherein the opioid agent is oxycodone.

14. A method of enhancing motility of the gastrointestinal tract in a mammal, the method comprising administering to the mammal a pharmaceutical composition comprising a pharmaceutically-acceptable carrier and a crystalline salt form which is the hydrate of the sulfate salt of 3-endo-(8-{2-[cyclohexylmethyl-((S)-2,3-dihydroxy-propionyl)amino]ethyl}-8-aza-bicyclo[3.2.1]oct-3-yl)benzamide wherein the crystalline salt form is characterized by an x-ray powder diffraction pattern having two or more diffraction peaks at 2θ values selected from 9.41±0.20, 9.98±0.20, 15.17±0.20, 16.70±0.20, 18.59±0.20, 19.46±0.20, 19.91±0.20, 20.63±0.20, 21.35±0.20, 21.89±0.20, 23.00±0.20, 24.20±0.20, 25.40±0.20, 26.03±0.20, 27.44±0.20, 28.46±0.20, 29.45±0.20, 31.22±0.20, 31.82±0.20, 33.17±0.20, 33.56±0.20, and 36.89±0.20.

15. The method of claim 14 wherein the x-ray powder diffraction pattern comprises two or more diffraction peaks at 2θ values selected from 16.70±0.20, 18.59±0.20, 19.46±0.20, 19.91±0.20, 23.00±0.20, and 24.20±0.20.

16. The method of claim 14, wherein the crystalline salt form is characterized by an x-ray powder diffraction pattern in which the peak positions are substantially in accordance with the peak positions of the pattern shown in FIG. 4.

17. The method of claim 14, wherein the crystalline salt form is characterized by a differential scanning calorimetry trace substantially in accordance with that shown in FIG. 5.

* * * * *